(12) United States Patent
Michal et al.

(10) Patent No.: US 8,741,326 B2
(45) Date of Patent: *Jun. 3, 2014

(54) MODIFIED TWO-COMPONENT GELATION SYSTEMS, METHODS OF USE AND METHODS OF MANUFACTURE

(75) Inventors: Gene Michal, San Francisco, CA (US); Shubhayu Basu, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1613 days.

This patent is subject to a terminal disclaimer.

(21) Appl. No.: 11/561,328

(22) Filed: Nov. 17, 2006

(65) Prior Publication Data

US 2008/0119385 A1    May 22, 2008

(51) Int. Cl.
*A61K 9/127* (2006.01)
*A61P 7/00* (2006.01)

(52) U.S. Cl.
USPC ............................ 424/423; 424/450; 424/491

(58) Field of Classification Search
None
See application file for complete search history.

(56) References Cited

U.S. PATENT DOCUMENTS

| | | |
|---|---|---|
| 2,512,569 A | 6/1950 | Saffir |
| 3,144,868 A | 8/1964 | Jascalevich |
| 3,584,624 A | 6/1971 | de Ciutiis |
| 3,780,733 A | 12/1973 | Martinez-Manzor |
| 3,804,097 A | 4/1974 | Rudie |
| 3,890,976 A | 6/1975 | Bazell et al. |
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,321,501 A | 6/1994 | Swanson et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling |
| 5,437,632 A | 8/1995 | Engelson |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |

(Continued)

FOREIGN PATENT DOCUMENTS

| | | |
|---|---|---|
| EP | 0835667 | 4/1998 |
| EP | 0861632 | 9/1998 |

(Continued)

OTHER PUBLICATIONS

Abbott Cardiovascular Systems Inc., PCT International Preliminary Report on Patentability and Written Opinion dated Dec. 24, 2008 for PCT/US2007/013181, 11 pages.
Abbott Cardiovascular Systems Inc, PCT International Search Report and Written Opinion mailed Feb. 10, 2009 for PCT Application No. PCT/US2007/023419, 17 pages.
Friedman, Paul M., et al., "Safety Data of Injectable Nonanimal Stabilized Hyaluronic Acid Gel for Soft Tissue Augmentation," Dermatologic Surgery, 2002, vol. 28, pp. 491-494.
Abbott Cardiovascular Systems, Office Action mailed Apr. 6, 2009 for U.S. Appl. No. 11/447,340.
Abbott Cardiovascular Systems, Office Action mailed Mar. 30, 2009 for U.S. Appl. No. 10/792,960.

(Continued)

*Primary Examiner* — Lisa J Hobbs
(74) *Attorney, Agent, or Firm* — Randy Shen; Blakely Sokoloff Taylor & Zafman LLP

(57) ABSTRACT

A bioscaffolding can be formed from a mixture of gel components of different gelation systems. For example, a bioscaffolding can be formed by mixing at least two different components of at least two different two-component gelation systems to form a first mixture and by mixing at least two different components (other than the components that make up the first mixture) of the at least two different two-component gelation systems to form a second mixture. A treatment agent, such as a cell type or a growth factor, can be added to either the first mixture or the second mixture. In some embodiments, the treatment agent is not added to either mixture. The first mixture can be co-injected with the second mixture to form a bioscaffolding in an infarct region for treatment thereof.

16 Claims, 5 Drawing Sheets

(56) References Cited

U.S. PATENT DOCUMENTS

| | | |
|---|---|---|
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A | 6/1998 | Glad et al. |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream et al. |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,068,599 A | 5/2000 | Saito et al. |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,152,141 A | 11/2000 | Stevens et al. |
| 6,153,428 A | 11/2000 | Gustafsson et al. |
| 6,159,443 A | 12/2000 | Hallahan et al. |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,464,862 B2 | 10/2002 | Bennett |
| 6,465,001 B1 | 10/2002 | Hubbell et al. |
| 6,478,775 B1 | 11/2002 | Galt et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,227 B2 | 4/2003 | Sahatjian et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,569,441 B2 | 5/2003 | Kunz et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,620,927 B2 | 9/2003 | Bulpitt et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,663,881 B2 | 12/2003 | Kunz et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,726,677 B1 | 4/2004 | Flaherty et al. |
| 6,726,923 B2 | 4/2004 | Iyer et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |

(56) References Cited

U.S. PATENT DOCUMENTS

| | | |
|---|---|---|
| 6,824,791 B2 | 11/2004 | Mathiowitz et al. |
| 6,858,229 B1 | 2/2005 | Hubbell et al. |
| 6,893,431 B2 | 5/2005 | Naimark et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1* | 1/2006 | Chang et al. .............. 530/354 |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,294,334 B1 | 11/2007 | Michal et al. |
| 7,361,360 B2 | 4/2008 | Kitabwalla et al. |
| 7,361,368 B2 | 4/2008 | Claude et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,641,643 B2 | 1/2010 | Michal et al. |
| 7,732,190 B2 | 6/2010 | Michal et al. |
| 7,815,590 B2 | 10/2010 | Cooper |
| 7,854,944 B2 | 12/2010 | Mandrusov et al. |
| 8,038,991 B1 | 10/2011 | Stankus et al. |
| 8,187,621 B2 | 5/2012 | Michal |
| 8,192,760 B2 | 6/2012 | Hossainy et al. |
| 8,221,744 B2 | 7/2012 | Basu et al. |
| 8,293,226 B1 | 10/2012 | Basu et al. |
| 8,303,972 B2 | 11/2012 | Michal |
| 8,383,158 B2 | 2/2013 | Michal et al. |
| 8,388,948 B2 | 3/2013 | Basu et al. |
| 8,486,386 B2 | 7/2013 | Michal et al. |
| 8,486,387 B2 | 7/2013 | Michal et al. |
| 8,500,680 B2 | 8/2013 | Claude et al. |
| 8,521,259 B2 | 8/2013 | Mandrusov et al. |
| 8,608,661 B1 | 12/2013 | Mandrusov et al. |
| 8,609,126 B2 | 12/2013 | Michal et al. |
| 2001/0023349 A1 | 9/2001 | Van Tassel et al. |
| 2001/0055615 A1 | 12/2001 | Wallace et al. |
| 2002/0006429 A1 | 1/2002 | Redmond et al. |
| 2002/0013408 A1 | 1/2002 | Rhee et al. |
| 2002/0042473 A1 | 4/2002 | Trollsas et al. |
| 2002/0076441 A1* | 6/2002 | Shih et al. .............. 424/484 |
| 2002/0077657 A1 | 6/2002 | Ginn et al. |
| 2002/0090725 A1* | 7/2002 | Simpson et al. .............. 435/402 |
| 2002/0102272 A1 | 8/2002 | Rosenthal et al. |
| 2002/0131974 A1 | 9/2002 | Segal |
| 2002/0142458 A1* | 10/2002 | Williams et al. .............. 435/366 |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0114505 A1 | 6/2003 | Nagao et al. |
| 2003/0125766 A1 | 7/2003 | Ding |
| 2003/0175410 A1* | 9/2003 | Campbell et al. .............. 427/2.24 |
| 2003/0233150 A1 | 12/2003 | Bourne et al. |
| 2004/0002650 A1 | 1/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu et al. |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0149392 A1* | 7/2006 | Hsieh et al. .............. 623/23.58 |
| 2007/0270948 A1* | 11/2007 | Wuh .............. 623/7 |
| 2008/0025943 A1 | 1/2008 | Michal et al. |
| 2009/0022817 A1 | 1/2009 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| FR | 2715855 | 8/1995 |
| GB | 2194144 | 3/1988 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001508666 | 7/2001 |
| JP | 2003062089 | 3/2003 |
| JP | 2006014570 | 1/2006 |
| JP | 2007009185 | 1/2007 |
| JP | 2006523507 | 10/2009 |
| WO | WO-9210142 | 6/1992 |
| WO | WO-9315781 | 8/1993 |
| WO | WO-9522316 | 8/1995 |
| WO | WO-9733633 | 9/1997 |
| WO | WO-9854301 | 12/1998 |
| WO | WO-9953943 | 10/1999 |
| WO | WO-0054661 | 9/2000 |
| WO | WO-0071196 | 11/2000 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03005961 | 1/2003 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-2004000915 | 12/2003 |
| WO | WO-2004050013 | 6/2004 |
| WO | WO-2004058305 | 7/2004 |
| WO | WO-2004060346 | 7/2004 |
| WO | WO-2004066829 | 8/2004 |
| WO | WO-2004091592 | 10/2004 |
| WO | WO-2004098669 | 11/2004 |
| WO | WO-2006014570 | 2/2006 |
| WO | WO-2006027549 | 3/2006 |
| WO | WO-2006113407 | 10/2006 |
| WO | WO-2007145909 | 12/2007 |

OTHER PUBLICATIONS

Abbott Cardiovascular Systems, Office Action mailed Apr. 13, 2009 for U.S. Appl. No. 11/566,643.

Elbert, D. L., et al., "Protein delivery from materials formed by self-selective conjugate addition reactions", Journal of Controlled Release, 76, (2001), 11-25.

Agocha, A. et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), (Apr. 1997), pp. 2233-2244.

Anderson, J. M. et al., "Biodegradation and biocompatibility of PLA and PLGA microspheres", Advanced Drug Delivery Reviews, 28, (1997), pp. 5-24.

Baxter, "FloSeal Matrix Hemostatic Sealant", downloaded from the Internet on Nov. 14, 2002, from: http://www.fusionmed.com/docs/surgeon/default.asp, 2 pages.

(56) References Cited

OTHER PUBLICATIONS

Berger et al., "Poly-L-cysteine", J. Am. Chem. Soc., 78(17), (Sep. 5, 1956), pp. 4483-4488.

Bernatowicz, M. et al., "Preparation of Boc-[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.

Boland, E. D. "Electrospinning Collagen and Elastin: Preliminary Vascular Tissue Engineering", Frontiers in Bioscience, vol. 9, (May 1, 2004), pp. 1422-1432.

Brust, G. "Polyimides", downloaded from the Internet at: http://www.pslc.ws/macrorg/imide.htm, (2005), 4 pages.

Buschmann, I. et al., "Arteriogenesis versus angiogenesis: Two mechanisms of vessel growth", News Physiol. Sci., vol. 14, (Jun. 1999), pp. 121-125.

Canderm Pharma, "Technical Dossier: Artecoll", downloaded from the Internet on Oct. 22, 2002 from: http://www.canderm.conn/artecoll/tech.html, 3 pages.

Caplan, M. J. et al., "Dependence on pH of polarized sorting of secreted proteins", Dept. of Cell Biology and Dept. of Pathology, Yale University School of Medicine, Nature, vol. 329, (Oct. 15, 1987), p. 630.

Carpino, L. et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.

Chandy et al., "The development of porous alginate/elastin/PEG composite matrix for cardiovascular engineering", Journal of Biomaterials Applications, vol. 17, (Apr. 2003), pp. 287-301.

Corbett, S. et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Creemers, E. et al., "Matrix Metalloproteinase Inhibition After Myocardial Infarction: A New Approach to Prevent Heart Failure?", Circ. Res., vol. 89, (2001), pp. 201-210.

Crivello et al., "Synthesis and Photoinitiated Cationic Polymerization of Monomers with the Silsesquioxane Core", J Polym Science: Part A: Polymer Chemistry, 35, (1997), pp. 407-425.

Davis, M. E. et al., "Injectable Self-Assembling Peptide Nanofibers Create Intramyocardial Microenvironments for Endothelial Cells", Circulation, 111, (Feb. 2005), pp. 442-450.

Dinbergs et al., "Cellular response to transforming growth factor-$\beta$1 and basic fibroblast growth factor depends on release kinetics and extracellular matrix interactions", The Journal of Biological Chemistry, vol. 271, No. 47, (Nov. 1996), pp. 29822-29829.

Edelman, "Controlled and modulated release of basic fibroblast growth factor", Biomaterials, vol. 12, (Sep. 1999), pp. 619-626.

Etzion, S. et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.

Fukumoto, S. et al., "Protein Kinase C $\delta$ Inhibits the Proliferation of Vascular Smooth Muscle Cells by Suppressing $G_1$ Cyclin Expression", The Journal of Biological Chemistry, 272(21), (May 1997), pp. 13816-13822.

Giordano, F. et al., "Angiogenesis: The Role of the Microenvironment in Flipping the Switch", Current Opinion in Genetics and Development, 11, (2001), pp. 35-40.

Gossler et al., "Transgenesis by means of blastocyst-derived embryonic stem cell lines", Natl. Acad. Sci. USA, 83, (Dec. 1986), pp. 9065-9069.

Grafe, T. H. "Nanofiber Webs from Electrospinning", Presented at the Nonwovens in Filtration—Fifth International Conference, Stuttgart, Germany, (Mar. 2003), pp. 1-5.

Grund, F. et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Gupta et al., "Changes in Passive Mechanical Stiffness of Myocardial Tissue with Aneurysm Formation", Circulation, 89(5), (May 1994), pp. 2315-2326.

Hashimoto, T. et al., "Development of Alginate Wound Dressings Linked with Hybrid Peptides Derived from Laminin and Elastin", Biomaterials, 25, (2004), pp. 1407-1414.

Haugland et al., "Dialkylcarbocyanine and Dialkylaminostryryl Probes", Handbook of Fluorescent Probes and Research Products, Molecular Probes, Inc., (2002), pp. 530-534.

Haugland et al., "Membrane-permeant reactive tracers", Handbook of Fluorescent Probes and Research Products, Molecular Probes, Inc., (2002), pp. 458-553.

Heeschen, C, et al., "Nicotine Stimulates Tumor Angiogenesis", American College of Cardiology, 37(2) Supplement A, (Feb. 2001), pp. 1A-648A, Abstract downloaded from the Internet at: http://24.132.160.238/ciw-01acc/abstract_search_author.cfm?SearchName=Heeschen, 1 page.

Helisch, A. et al., "Angiogenesis and arteriogenesis—not yet for prescription", NEUE Diagnostische Und Therap. Verfahren, Z Kardiol, 89, (2000), pp. 239-244.

Hendel, R. C. et al., "Effect of Intracoronary Recombinant Human Vascular Endothelial Growth Factor on Myocardial Perfusion: Evidence for a Dose-Dependent Effect", Circulation, 101, (2000), pp. 118-121.

Huang, K. et al., "Synthesis and Characterization of Self-Assembling Block Copolymers Containing Bioadhesive End Groups", Biomacromolecules, 3(2), (2002), pp. 397-406.

Hutcheson, K. et al., "Comparison of Benefits on Myocardial Performance of Cellular Cardiomyoplasty with Skeletal Myoblasts and Fibroblasts", Cell Transplantation, 9(3), (2000), pp. 359-368.

Ito, W. D. et al., "Monocyte chemotactic protein-1 increases collateral and peripheral conductance after femoral artery occlusion", Max-Planck-Institute for Physiological and Clinical Research, Bad Nauheim, Germany, (Feb. 21, 1997), pp. 829-837.

Johnson et al., "The stabilization and encapsulation of human growth hormone into biodegradable microspheres", Pharmaceutical Research, vol. 14, No. 6, (1997), pp. 730-735.

Kalltorp, M. et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), pp. 251-259.

Kawai et al., "Accelerated tissue regeneration through incorporation of basic fibroblast growth factor-impregnated gelatin microspheres into artificial dermis", Biomaterials, 21(5), (Mar. 2002), pp. 489-499.

Kelley et al., "Restraining Infarct Expansion Preserves Left Ventricular Geometry and Function After Acute Anteroapical Infarction", Circulation, 99, (1999), pp. 135-142.

Kelly, E. B. "Advances in Mammalian and Stem Cell Cloning", Genetic Engineering News, vol. 23, No. 7, (Apr. 1, 2003), pp. 17-18 & 68.

Kim, D. et al., "Glow Discharge Plasma Deposition (GDPD) Technique for the Local Controlled Delivery of Hirudin from Biomaterials", Pharmaceutical Research, 15(5), (1998), pp. 783-786.

Kipshidze, N. et al., "Therapeutic angiogenesis for critical limb ischemia to limit or avoid amputation", University of Wisconsin Medical School, The Journal of Invasive Cardiology, vol. 11, No. 1, (Jan. 1999), pp. 25-28.

Klugherz, B. D. et al., "Gene delivery from a DNA controlled-release stent in porcine coronary arteries", Nature Biotechnology, vol. 18, (Nov. 2000), pp. 1181-1184.

Kohilas, K. et al., "Effect of prosthetic titanium wear debris on mitogen-induced monocyte and lymphoid activation", John Hopkins University, Dept. of Orthopaedic Surgery, (Apr. 1999), pp. 95-103.

Kwok, C. et al., "Design of Infection-Resistant Antibiotic-Releasing Polymers: I. Fabrication and Formulation", Journal of Controlled Release, 62, (1999), pp. 289-299.

Laham, R. J. "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leibovich, S. J. et al., "Macrophage-Induced Angiogenesis is Mediated by Tumour Necrosis Factor-$\alpha$", Nature, vol. 329, (Oct. 15, 1987), pp. 630-632.

(56) References Cited

OTHER PUBLICATIONS

Leor, J. et al., "Bioengineered Cardiac Grafts-A New Approach to Repair the Infarcted Myocardium?", Circulation, 102[suppl III], (2000), pp. III-56-III-61.
Li, J. et al., "PR39, A Peptide Regulator of Angiogenesis", Nature Medicine, 6(1), (Jan. 2000), pp. 49-55.
Li., Y. Y. et al., "Differential Expression of Tissue Inhibitors of Metalloproteinases in the Failing Human Heart", Circulation, 98(17), (1998), pp. 1728-1734.
Lindsey, M. et al., "Selective Matrix Metalloproteinase Inhibition Reduces Left Ventricular Remodeling but does not Inhibit Angiogenesis after Myocardial Infarction", Circulation, 105(6), (2002), pp. 753-758.
Lopez, J. J. et al., "Angiogenic potential of perivascular delivered aFGF in a porcine model of chronic myocardial ischemia", The American Physiological Society, 0363-6135/98, (1998), pp. H930-H936.
Lu, L. et al., "Biodegradable Polymer Scaffolds for Cartilage Tissue Engineering", Clinical Orthopaedics and Related Research, Carl T. Brighton (ed.). No. 391S, (2001), pp. S251-S270.
Luo, Y. et al., "Cross-linked Hyaluronic Acid Hydrogel Films: New Biomaterials for Drug Delivery", Journal of Controlled Release, 69, (2000), pp. 169-184.
Lyman, M. D. et al., "Characterization of the Formation of Interfacially Photopolymerized Thin Hydrogels in Contact with Arterial Tissue", Biomaterials, 17(3), (1996), pp. 359-364.
Nguyen, K. T. et al., "Photopolymerizable Hydrogels for Tissue Engineering Applications", Biomaterials, 23, (2002), pp. 4307-4314.
Nikolic, S. D. et al., "New Angiogenic Implant Therapy Improves Function of the Ischemic Left Venticle", Supplement to Circulation; Abstracts From Scientific Sessions 2000, 102(18), (Oct. 2000), pp. II-689, Abstract 3331.
Nose et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.
Ohyanagi, H. et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.
Ozbas-Turan, S. "Controlled Release of Interleukin-2 from Chitosan Microspheres", Journal of Pharmaceutical Sciences, 91(5), (May 2002), pp. 1245-1251.
Rowley et al., "Alginate Hydrogels as Synthetic Extracelllular Matrix Materials", Biomaterials, 20(1), (1999), pp. 45-53.
Sawhney, A. S. et al., "Bioerodible Hydrogels Based on Photopolymerized Poly(ethylene glycol)-co-poly(a-hydroxy acid) Diacrylate Macromers", Macromolecules, 26(4), (1993), pp. 581-587.
Shin, H. et al., "In vivo bone and soft tissue response to injectable, biodegradable oligo(poly(ethylene glycol) fumarate) hydrogels", Biomaterials, 24, Elseview Science Ltd., (2003), pp. 3201-3211.
Simons, M. et al., "Clinical trials in coronary angiogenesis: Issues, problems, consensus, An expert panel summary", Angiogenesis Research Center, American Heart Association, Inc., (Sep. 12, 2000), pp. 1-14.
Spenlehauer, G. et al., "In vitro and in vivo degradation of poly(D,L lactide/glycolide) type microspheres made by solvent evaporation method", Biomaterials, vol. 10, (Oct. 1989), pp. 557-563.
Spinale, F. G. "Matrix Metalloproteinases—Regulation and Dysregulation in the Failing Heart", Circ. Res., 90, (2002), pp. 520-530.
Van Der Giessen, W. J. et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), pp. 1690-1697.
Visscher, G.E. et al., "Tissue response to biodegradable injectable microcapsules", Journal of Biomaterials Applications, vol. 2, (Jul. 1987), pp. 118-119.

Yamomoto, N. et al., "Histologic evidence that basic fibroblast growth factor enhances the angiogenic effects of transmyocardial laser revascularization", Basic Research in Cardiology, vol. 95, No. 1, (Feb. 1, 2000), pp. 55-63.
Zervas, L. et al., "On Cysteine and Cystine Peptides. II. S-Acylcysteines in Peptide Synthesis", J. Am. Chem. Soc., 85(9), (May 1963), pp. 1337-1341.
Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.
Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.
Leibovich, S. J., et al., "Macrophage-induced angiogenesis is mediated by tumour necrosis factor-alpha", Depts. of Oral Biology and Pathology, Northwestern University Dental School, Nature, vol. 329, (Oct. 15, 1997), 630-633.
Nikolic, S. D., et al., "Novel means to improve coronary blood flow", Clinical Science, Abstracts from Scientific Sessions, (2000), II-689.
Shu, et al., "Disulfide-crosslinked hyaluronan-gelatin hydrogel films: a covalent mimic of the extracellular matrix for in vitro cell growth", Biomaterials, 24(21), Abstract downloaded from the Internet at: http://www.sciencedirect.com, 1 page, (Sep. 2003), pp. 3825-3834.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, Office Action dated May 12, 2009 for U.S. Appl. No. 11/496,824.
Abbott Cardiovascular Systems, Non-Final Office Action dated Mar. 13, 2009 for U.S. Appl. No. 10/414,602.
Abbott Cardiovascular Systems, International search report and written opinion dated Jun. 18, 2009 for PCT/US2008/051505.
Abbott Cardiovascular Systems, Office Action dated Apr. 29, 2009 for U.S. Appl. No. 12/013,286.
Staatz, WD, et al., "Identification of a tetrapeptide recognition sequence for the alpha 2 beta 1 integrin in collagen", Journal of Biological Chemistry, 1991, 266(12), pp. 7363-7367.
Zheng, Shu, et al., "In situ crosslinkable hyaluronan hydrogels for tissue engineering", Biomaterials, Elsevier Science Publishers, vol. 25, No. 7-8, (2004), 1339-1348.
Abbott Cardiovascular Systems, Non final office action dated Apr. 14, 2010 for U.S. Appl. No. 12/016,180.
Abbott Cardiovascular Systems, Final office action dated Apr. 22, 2010 for U.S. Appl. No. 10/414,602.
Abbott Cardiovascular Systems, Non final office action dated Apr. 29, 2010 for U.S. Appl. No. 10/792,960.
Abbott Cardiovascular Systems, Non-Final Office Action dated Jun. 4, 2010 for U.S. Appl. No. 10/781,984.
Abbott Cardiovascular Systems, Non final office action dated Aug. 13, 2010 for U.S. Appl. No. 11/447,340.
Abbott Cardiovascular Systems, Final office action dated Sep. 27, 2010 for U.S. Appl. No. 10/792,960.
Hao, X, et al., "Angiogenic effects of sequential release of VEGF-A165 and PDGF-BB with alginate hydrogels after myocardial infarction", Cardiovascular Research, 75, (2007), 178-185.

(56) References Cited

OTHER PUBLICATIONS

Ritter, A. B., et al., "Elastic modulus, distensibility, and compliance (capacitance)", Biomedical Engineering Principles, Chapter 4, (2005), 187-191.
Abbott Cardiovascular Systems, Non-Final Office Action dated Mar. 5, 2009 for U.S. Appl. No. 11/507,860.
Abbott Cardiovascular Systems, Non final office action dated Aug. 5, 2009 for U.S. Appl. No. 11/031,608.
Abbott Cardiovascular Systems, Final office action dated Mar. 29, 2010 for U.S. Appl. No. 11/031,608.
Abbott Cardiovascular Systems, Final Office Action mailed Jul. 15, 2010, U.S. Appl. No. 11/507,860.
Abbott Cardiovascular Systems, Non final office action mailed Jun. 7, 2011 for U.S. Appl. No. 11/447,340.
Abbott Cardiovascular Systems, Non final office action mailed Jul. 6, 2011 for U.S. Appl. No. 10/781,984.
Abbott Cardiovascular Systems, Final office action mailed Jun. 28, 2011 for U.S. Appl. No. 10/792,960.
Abbott Cardiovascular Systems, Final office action mailed Jul. 18, 2011 for U.S. Appl. No. 11/566,643.
Abbott Cardiovascular Systems, Non-Final Office Action mailed Aug. 31, 2011 for U.S. Appl. No. 11/110,223.
Abbott Cardiovascular Systems, Final office action mailed Sep. 20, 2011 for U.S. Appl. No. 11/938,752.
Abbott Cardiovascular Systems, Final Office Action mailed Oct. 21, 2011 for U.S. Appl. No. 10/781,984.
Abbott Cardiovascular Systems, Non final office action mailed Nov. 8, 2011 for U.S. Appl. No. 10/792,960.
Abbott Cardiovascular Systems, Final Office Action mailed Dec. 13, 2011 for U.S. Appl. No. 12/963,397.
Abbott Cardiovascular Systems, Final Office Action mailed Jan. 5, 2012 for U.S. Appl. No. 11/361,920.
Abbott Cardiovascular Systems, Office Action mailed Jan. 17, 2012 for European Patent Application 08727952.7, 6 pages.
Abbott Cardiovascular Systems, Non-Final Office Action mailed Jan. 30, 2012 for U.S. Appl. No. 10/781,984.
Abbott Cardiovascular Systems, Final Office Action mailed Feb. 8, 2012 for Japanese application No. 2006-509975, 6 pages.
Abbott Cardiovascular Systems, Non-Final Office Action mailed Feb. 15, 2012 for U.S. Appl. No. 12/114,717.
Abbott Cardiovascular Systems Final Office Action mailed Apr. 4, 2012 for U.S. Appl. No. 10/792,960.
Abbott Cardiovascular Systems, European Office Action mailed Apr. 11, 2012 for App No. 12155231.9, 9 pages.
Abbott Cardiovascular Systems, European Office Action mailed Apr. 10, 2012 for App No. 07810637.4, 6 pages.
Abbott Cardiovascular Systems, Final Office Action mailed May 9, 2012 for U.S. Appl. No. 11/110,223.
Abbott Cardiovascular Systems, European Search report for application No. 12151788.2 mailed Apr. 18, 2012, 6 pages.
Abbott Cardiovascular Systems, Non-final Office Action mailed Jun. 22, 2012 for U.S. Appl. No. 12/963,397.
Abbott Cardiovascular Systems, Restriction requirement mailed Jul. 3, 2012 for U.S. Appl. No. 13/4722,324.
Abbott Cardiovascular Systems, Non-Final Office Action mailed Jun. 26, 2012 for U.S. Appl. No. 12/632,612.
Abbott Cardiovascular Systems, Japanese Office Action dated Jun. 11, 2012 for Appln. No. 2010-162711.
Abbott Cardiovascular Systems, Non-final Office Action mailed Aug. 28, 2012 for U.S. Appl. No. 13/472,324.
Abbott Cardiovascular Systems, Non-final Office Action mailed Aug. 30, 2012 for U.S. Appl. No. 13/472,328.
Abbott Cardiovascular Systems, Non-Final Office Action Sep. 11, 2012 for U.S. Appl. No. 10/792,960.
Abbott Cardiovascular Systems, Japanese office action dated Aug. 20, 2012 for JP 2009-537153.
Abbott Cardiovascular Systems, Non-Final Office Action dated Oct. 3, 2012 for U.S. Appl. No. 12/756,119.
Abbott Cardiovascular Systems, Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Abbott Cardiovascular Systems, Japanese Office Action dated Nov. 19, 2012 for Appln. No. 2009-539265.
Abbott Cardiovascular Systems, Final office action dated Jan. 18, 2013 for U.S. Appl. No. 12/963,397.
Abbott Cardiovascular Systems, Japanese office action dated Oct. 9, 2012 for JP Appln. No. 2009-514330.
Abbott Cardiovascular Systems, Japanese Office Action mailed Dec. 17, 2012 for JP Appln. No. 2009-546553.
Abbott Cardiovascular Systems, Examination Report dated Feb. 20, 2013 for European Appln. No. 12151788.2, 4 pages.
Abbott Cardiovascular Systems, Non final office action dated Apr. 1, 2013 for U.S. Appl. No. 13/559,423.
Abbott Cardiovascular Systems, Non-Final Office Action dated Oct. 3, 2012 for U.S. Appl. No. 12/756,092.
Abbott Cardiovascular Systems, Final Office Action mailed Apr. 15, 2011 for U.S. Appl. No. 10/414,602.
Advanced Cardiovascular Systems, Extended EP Search Report dated May 20, 2011 for EP Application No. 10186197.9.
Advanced Cardiovascular Systems, Extended European search report dated Apr. 21, 2011 for EP Application No. 10186186.2.
Bull, S., et al., "Self-Assembled Peptide Amphiphile Nanofibers Conjugated to MRI Contrast Agents", Nano Letters, vol. 5, No. 1, (Jan. 2005), 4 pages.
Chung, Y., et al., "Sol-gel transition temperature of PLGA-g-PEG aqueous solutions", Biomacromolecules, vol. 3, No. 3, (May 2002), 511-516.
Csonka, E., et al., "Interspecific Interaction of Aortic Endothelial and Smooth Muscle Cells", Acta Morphologica Hungarica, vol. 35, No. 1-2, (1987), 31-35.
Davis, M E., et al., "Injectable Self-Assembling Peptide Nanofibers Create Intramyocardial Microenvironments for Endothelial Cells", Circulation, 111, (2005), 442-450.
Griese, D. P., et al., "Vascular gene delivery of anticoagulants by transplantation of retrovirally-transduced endothelial progenitor cells", Cardiovascular Research, vol. 58, (2003), 469-477.
Hao, X, et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.
Hartgerink, J. D., et al., "Peptide-amphiphile nanofibers: A versatile scaffold for the preparation of self-assembling materials", PNAS, vol. 99, No. 8, (Apr. 16, 2002), 5133-5138.
Hartgerink, J. D., et al., "Self-Assembly and Mineralization of Peptide-Amphiphile Nanofibers", Science, vol. 294, (Nov. 23, 2001), 1684-1688.
Li, B., et al., "VEGF and PlGF promote adult vasculogenesis by enhancing EPC recruitment and vessel formation at the site of tumor neovascularization", The FASEB Journal, vol. 20, (2006), 1495-1497.
Mogan, L., "Rationale of platelet gel to augment adaptive remodeling of the injured heart", J Extra Corpor Technol, 36(2), (Jun. 2004), 191-196.
Seeger, J. M., et al., "Improved in vivo endothelialization of prosthetic grafts by surface modification with fibronectin", J Vasc Surg, vol. 8, No. 4, (Oct. 1988), 476-482 (Abstract ony).
Urbich, C., et al., "Endothelial Progenitor Cells: Characterization and Role in Vascular Biology", Circulation Research, vol. 95, (2004), 343-353.
Zheng, W., "Mechanisms of coronary angiogenesis in response to stretch; role of VEGF and TGF-Beta", AM J Physiol Heart Circ Physiol 280(2), (Feb. 2001), H909-H917.
Abbott Cardiovascular Systems, Final office action mailed Sep. 27, 2010 for U.S. Appl. No. 12/016,180.
Abbott Cardiovascular Systems, Non final office action mailed May 31, 2013 for U.S. Appl. No. 13/559,438.
Abbott Cardiovascular Systems, Non final office action mailed Jul. 2, 2013 for U.S. Appl. No. 11/938,752.
Abbott Cardiovascular Systems, Final office action mailed Apr. 22, 2013 for U.S. Appl. No. 10/792,960.

(56) References Cited

OTHER PUBLICATIONS

Abbott Cardiovascular Systems, Japanese office action mailed Mar. 25, 2013 for JP 2009-539265.

Abbott Cardiovascular Systems, Final Office Action mailed Nov. 22, 2010 for U.S. Appl. No. 10/781,984, 13 pages.

Abbott Cardiovascular Systems, Non-final Office Action mailed Nov. 24, 2010 for U.S. Appl. No. 13/013,286, 11 pages.

Abbott Cardiovascular Systems, Non-final Office Action mailed Dec. 8, 2010 for U.S. Appl. No. 11/566,643, 17 pages.

Abbott Cardiovascular Systems, Non-final Office Action mailed Dec. 10, 2010 for U.S. Appl. No. 11/938,752, 32 pages.

Abbott Cardiovascular Systems, Non-final Office Action mailed Dec. 17, 2010 for U.S. Appl. No. 11/933,922, 23 pages.

Abbott Cardiovascular Systems, website for HEALON (R) OVD, copyright 2010, accessed Dec. 15, 2010, URL: <http://abbottmedicaloptics.com/products/cataract/ovds/healon-viscoelastic>, (2010), 2 pages.

Abbott Cardiovascular Systems, Product Information Sheet for HEALON (R), from Abbott Medical Optics, (2005), 1 page.

Abbott Cardiovascular Systems, Japanese Office Action dated Dec. 8, 2010 for Japanese Patent App No. 2006-509975., 6 pages.

Abbott Cardiovascular Systems, Non final office action mailed Feb. 8, 2011 for U.S. Appl. No. 10/795,960.

Haynesworth, Stephen E., et al., "Platelet Effects on Human Mesenchymal Stem Cells", Abstract, presented at Orthopaedic Research Society 48th Annual Meeting, Dallas, TX, (Feb. 10-13, 2010), 2 pages.

Abbott Cardiovascular Systems, Non-Final Office Action mailed Dec. 4, 2013 for U.S. Appl. No. 11/507,860.

Abbott Cardiovascular Systems, Non-Final Office Action dated Aug. 20, 2013 for U.S. Appl. No. 12/114,717.

Abbott Cardiovascular Systems, Non-Final Office Action mailed Oct. 16, 2013 for U.S. Appl. No. 13/468,956.

Abbott Cardiovascular Systems, Non-Final Office Action mailed Oct. 23, 2013 for U.S. Appl. No. 11/110,223.

Abbott Cardiovascular Systems, Notice of Allowance mailed Sep. 30, 2013 for U.S. Appl. No. 13/559,423.

Abbott Cardiovascular Systems, Notice of Allowance mailed Dec. 23, 2013 for U.S. Appl. No. 13/559,438.

Abbott Cardiovascular Systems, Japanese office action mailed Nov. 22, 2013 for JP 2009-539265 (10 pages).

chemcas.org, MSDS 4-amino-2,2,6,6-tetramethlypiperidine-1-oxyl (4-amino-TEMPO) CAS No. 14691-88-4 at www.chemcas.org/drug/analytical/cas/14691-88-4-asp, (Sep. 2, 1997), 5 pages.

\* cited by examiner

MODIFIED TWO-COMPONENT GELATION SYSTEMS, METHODS OF USE AND METHODS OF MANUFACTURE

FIELD OF INVENTION

Post-myocardial infarction treatments and compositions.

SEQUENCE LISTING

An electronic copy of the Sequence Listing entitled "5618P5128_SeqList_ST25" is incorporated herein by reference. This Sequence Listing consists of [SEQ ID NOs: 1-3].

BACKGROUND OF INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that often results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arteries. An example of a mechanical procedure includes balloon angioplasty with stenting, while an example of a therapeutic agent application includes the administration of a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infarcted region and the healthy tissue resulting in uneven stress and strain distribution in the left ventricle. Once an MI occurs, remodeling of the heart begins. The principle components of the remodeling event include myocyte death, edema and inflammation, followed by fibroblast infiltration and collagen deposition, and finally scar formation from extra-cellular matrix (ECM) deposition. The principle component of the scar is collagen which is non-contractile and causes strain on the heart with each beat. Non-contractility causes poor pump performance as seen by low ejection fraction (EF) and akinetic or diskinetic local wall motion. Low EF leads to high residual blood volume in the ventricle, causes additional wall stress and leads to eventual infarct expansion via scar stretching and thinning and border-zone cell apoptosis. In addition, the remote-zone thickens as a result of higher stress which impairs systolic pumping while the infarct region experiences significant thinning because mature myocytes of an adult are not regenerated. Myocyte loss is a major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes also correlate with physiological changes that result in increase in blood pressure and worsening systolic and diastolic performance.

SUMMARY OF INVENTION

A bioscaffolding can be formed from a mixture of gel components of different gelation systems. In some embodiments, a bioscaffolding can be formed by mixing at least two different components (which do not gel upon mixing) of at least two different two-component gelation systems to form a first mixture and by mixing at least two different components (other than the components that make up the first mixture and which do not gel upon mixing) of the at least two different two-component gelation systems to form a second mixture. A treatment agent, such as a cell type or a growth factor, can be added to either the first mixture or the second mixture. The first mixture can then be co-injected with the second mixture to form a bioscaffolding in an infarct region for treatment thereof. The first and second mixtures can be co-injected with a dual-lumen delivery device, which can include, but are not limited to, a dual syringe, a dual-needle left-ventricle injection device, a dual-needle transvascular wall injection device and the like.

In some embodiments, a bioscaffolding can be formed by mixing at least two different gelation components (which do not gel upon mixing) to form a first mixture. A treatment agent, such as a cell type or a growth factor, can be added to the first mixture. The first mixture can then be co-injected with a second gelation component to form a bioscaffolding on or within an infarct region for treatment thereof. The first mixture and the gelation component can be co-injected with, a dual-lumen delivery device, which can include, but are not limited to, a dual syringes a dual-needle left-ventricle injection device, a dual-needle transvascular wall injection device and the like.

DETAILED DESCRIPTION

Figure 1:
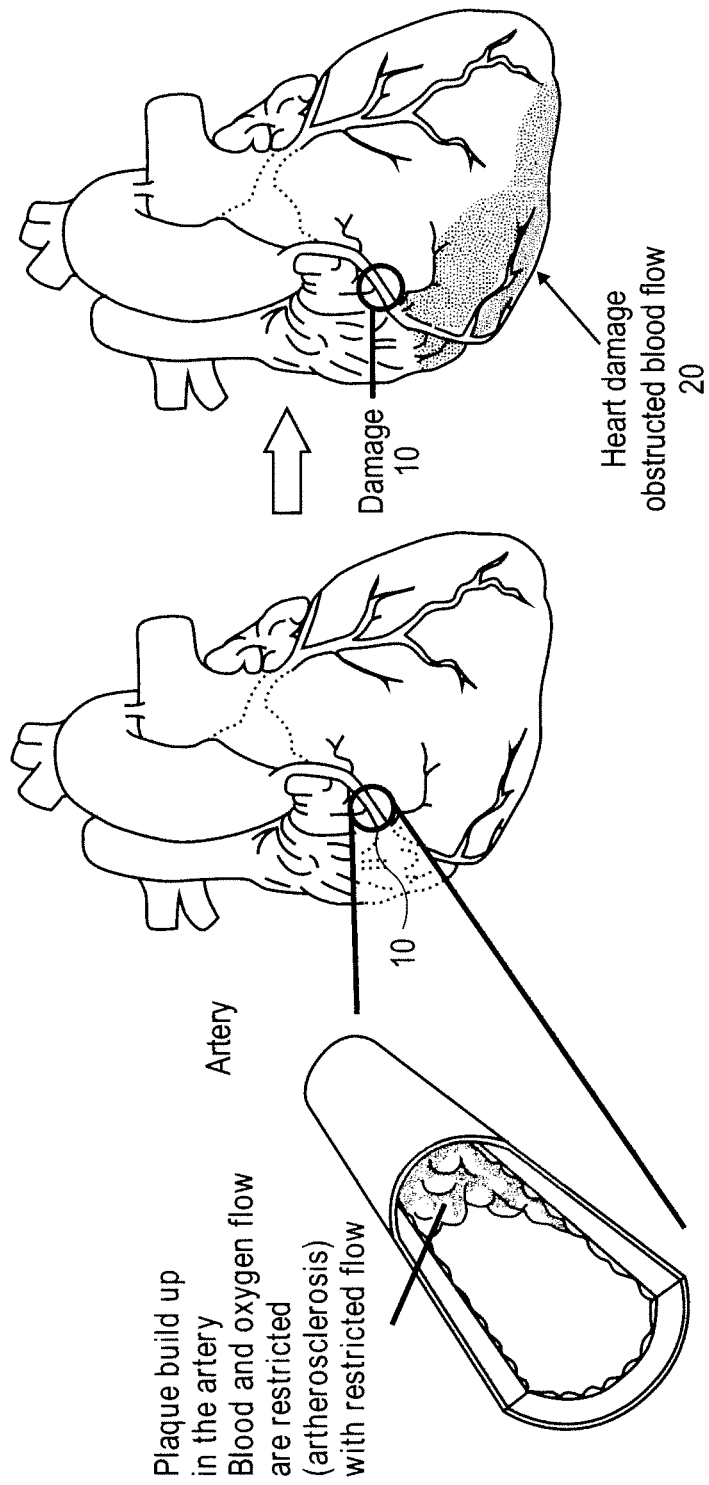
FIGS. 1A-1B illustrate the progression of heart damage once the build-up of plaque in an artery induces an infarct to occur.

FIGS. 1A-1B illustrate the progression of heart damage once the build-up of plaque induces an infarct to occur. FIG.

1A illustrates a site 10 where blockage and restricted blood flow can occur from, for example, a thrombus or embolus. FIG. 1B illustrates resultant damage area 20 to the left ventricle that can result from the lack of oxygen and nutrient flow carried by the blood to the inferior region left of the heart. The damage area 20 will likely undergo remodeling, and eventually scarring, resulting in a non-functional area.

Bioscaffoldings formed of two components and applied in situ to the left heart ventricle can be used to treat post-myocardial infarction tissue damage. "Bioscaffolding" and "two-component gelation system" and "gelation system" are hereinafter used interchangeably. Examples of two-component gelation systems include, but are not limited to, alginate construct systems, fibrin glues and fibrin glue-like systems, self-assembled peptides and combinations thereof. Each component of the two-component gelation system may be co-injected to an infarct region by a dual-lumen delivery device. Examples of dual-lumen delivery devices include, but are not limited to, a dual syringe, dual-needle left-ventricle injection devices, dual-needle transvascular wall injection devices and the like.

In some embodiments, at least one cell type may be co-injected with at least one component of the two-component gelation system to an infarct region. In some embodiments, the cells may be mixed with at least one component of the two-component gelation system before the two-components are co-injected to the infarct region. Examples of cell types, include, but are not limited to, localized cardiac progenitor cells, mesenchymal stem cells, bone marrow derived mononuclear cells, adipose stem cells, embryonic stem cells, umbilical cord blood derived stem cells, smooth muscle cells or skeletal myoblasts.

In some applications, the two-component gelation system includes a fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevent fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the infarct region. Fibrin glue can undergo gelation between about 5 to about 60 seconds. Examples of other fibrin glue-like systems include, but are not limited to, Tisseel™ (Baxter), Beriplast P™ (Aventis Behring), Biocol® (LFB, France), Crosseal™ (Omrix Biopharmaceuticals, Ltd.), Hemaseel HMN® (Haemacure Corp.), Bolheal (Kaketsuken Pharma, Japan) and CoStasis® (Angiotech Pharmaceuticals).

In some applications, the two-component gelation system includes self-assembled peptides. Self-assembled peptides generally include repeat sequences of alternating hydrophobic and hydrophilic amino acid chains. The hydrophilic amino acids are generally charge-bearing and can be anionic, cationic or both. Examples of cationic amino acids are lysine and arginine. Examples of anionic amino acids are aspartic acid and glutamic acid. Examples of hydrophobic amino acids are alanine, valine, leucine, isoleucine or phenylalanine. Self-assembled peptides can range from 8 to 40 amino acids in length and can assemble into nanoscale fibers under conditions of physiological pH and osmolarity. In sufficient concentration and over time, the fibers can assemble into an interconnected structure that appears macroscopically as a gel. Self-assembled peptides typically undergo gelation between several minutes to several hours. Examples of self-assembled peptides include, but are not limited to: AcN-RARADADARARADADA-CNH$_2$ (SEQ ID NO: 1) (RAD 16-II) wherein R is arginine, A is alanine, D is aspartic acid, and Ac indicates acetylation; VKVKVKVKV-PP-TKVKVKVKV-NH$_2$ (SEQ ID NO: 2) (MAX-1) wherein V is valine, K is lysine and P is proline; and AcN-AEAEAKA-KAEAEAKAK-CNH$_2$ (SEQ ID NO: 3) wherein A is alanine, K is lysine and E is glutamic acid (EAK 16-II). Self-assembled peptides show good cytocompatibility, as represented by cell adhesion, cell migration and proliferation.

In some applications, the two-component gelation system is an alginate construct system. One component may be an alginate conjugate (or alginate alone) which can include alginate and a protein constituent. The second component may be a salt. Examples of alginate conjugates can include, but are not limited to, alginate-collagen, alginate-laminin, alginate-elastin, alginate-collagen-laminin and alginate-hyaluronic acid in which the collagen, laminin, elastin, collagen-laminin or hyaluronic acid is covalently bonded (or not bonded) to alginate. Examples of salts which can be used to gel the alginate constructs include, but are not limited to, calcium chloride ($CaCl_2$), barium chloride ($BaCl_2$) or strontium chloride ($SrCl_2$).

In one embodiment, the alginate construct is alginate-gelatin. The molecular weight of the gelatin may be in the approximate range of 5 kDa to 100 kDa. The relatively low molecular weight of gelatin offers processing advantages in that it is more soluble and has lower viscosity than hydrogels of higher molecular weight. Another advantage of gelatin is that it contains from 1 to 4 RGD (arginine-glycine-aspartic acid peptide sequence) sites per molecule. RGD is a common cell adhesion ligand and would increase the retention of cells within the infarct zone where the bioscaffolding is formed. The cells retained by the RGD sites may be cells co-injected with the bioscaffolding components or dispersed throughout a component of the system.

The gelatin may be a porcine gelatin or a recombinant human gelatin. The porcine gelatin is a hydrolyzed type 1 collagen extracted from porcine skin. In one embodiment, the molecular weight of the porcine gelatin is approximately 20 kDa. The human gelatin is produced by bacteria using human genetic material. The human recombinant gelatin is equivalent to the porcine gelatin but may reduce the likelihood of an immune response when injected into an infarct region of a human subject.

Alginate is a linear polysaccharide derived from seaweed and contains mannuronic (M) and gluronic acid (G), presented in both alternating blocks and alternating individual residues. It is possible to use some of the carboxyl groups of the alginate as sites to graft useful cell adhesion ligands, such as collagen, laminin, elastin and other peptide fragments of the ECM matrix, forming an alginate conjugate, because alginate does not have RGD groups for cell retention.

An alginate-gelatin conjugate is valuable because it combines characteristics of alginate with characteristics of gelatin, which include, but are not limited to, RGD sites and immunocompatibility. Characteristics of alginate include rapid, almost instantaneous gelation, and an inflammation stimulating effect. The alginate-gelatin conjugate can be formed of approximately 1% to 30% and more particularly approximately 10% to 20% gelatin (either porcine or human recombinant) and approximately 80% to 90% alginate. The relatively lower proportion of alginate-gelatin conjugate is used to retain gelation capacity once combined with pure alginate because the alginate carboxyl groups of alginate that cause the gelation may be bound up in the alginate-gelatin conjugate.

Two-component gelation systems exhibit different characteristics relative to one another including, but not limited to, pore size, storage modulus and gelation time. The gelation system behaves as a sieving media and therefore includes small pores. "Pore size" refers to small, vacuous openings within the gel. "Storage modulus" refers to the strength or the stiffness of the material upon gelation. Storage modulus can be measured by a rheometric instrument. "Gelation time" refers to the kinetics of gelation. Alginate constructs can gel within about 1 second, while fibrin glues can gel between about 5 seconds and about 60 seconds. Self-assembled peptides typically undergo gelation between several minutes to several hours.

In embodiments in which cells are co-injected with the two-component gelation system, or mixed with one component before combining the two components, the gelation system can exhibit different characteristics relative to one another relating to the cells. Such characteristics can include, but are not limited to, morphology of the cells, cell survivability, encapsulation efficiency and/or cell concentration. "Morphology" refers to the physical structure of the cells. In the case of hMSC, the natural morphology is a flattened spindle-shaped morphology. "Cell survivability" is the amount of time that the cells remain viable within the gel post-injection. "Encapsulation efficiency" refers to the fraction of the initial number of cells in suspension that are entrapped within the gel. "Cell concentration" is the encapsulation efficiency divided by the volume of gel formed.

A characteristic which affects the encapsulation efficiency is the difference in viscosity ($\eta$) of the two components. If the difference in viscosity between the two components of the gelation system is large, then the encapsulation efficiency is high only when cells are in the high viscosity component. However, if the viscosity of each individual component is lowered without compromising the gelation kinetics, the encapsulation efficiency increases dramatically. For a catheter-based delivery system, low viscosity components are very helpful for successful delivery. A successful application of the two components (which are in solution before delivery) can be dependent upon low viscosity of the individual components.

Modified Gelation Systems

In some embodiments, a bioscaffolding can be formed from a mixture of gel components of different gelation systems. For example, a bioscaffolding can be formed by mixing at least two different components (which do not gel upon mixing under standard cath lab process conditions) of at least two different two-component gelation systems to form a first mixture, and, by mixing at least two different components (other than the components that make up the first mixture and which do not gel upon mixing under standard cath lab process conditions) of the at least two different two-component gelation systems to form a second mixture. "Gel" refers to the phase change from a liquid to a solid upon the combination of two different components or two different mixtures. A treatment agent, such as a cell type or a growth factor, can be added to either the first mixture or the second mixture. The first mixture can then be co-injected with the second mixture to form a bioscaffolding in an infarct region for treatment thereof. In some embodiments, a bioscaffolding can be formed by mixing at least two different gelation components (which do not gel upon mixing under standard cath lab process conditions) to form a first mixture. A treatment agent, such as a cell type or a growth factor, can be added to the first mixture. The first mixture can then be co-injected with a gelation component to form a bioscaffolding on an infarct region for treatment thereof. In some embodiments, the treatment agent can be co-injected with the first mixture or the gelation component without first interdispersing the treatment agent within the first mixture or the gelation component.

In some embodiments, an alginate construct system can include an alginate-gelatin solution as a first component and a calcium chloride solution as a second component. In some embodiments, human mesenchymal stems cells (hMSC) are suspended in one component of the gelation system. hMSC are thought to be capable of both self renewal and differentiation into bone, cartilage, muscle, tendon and fat. hMSC also give rise to a variety of mature cell types via a step-wise maturation process called mesengenesis. The natural morphology of hMSC is elongated and spindle shaped. The gelatin provides RGD sites for cellular adhesion i.e. adhesion of hMSC. Alginate construct systems exhibit rapid gelling kinetics. When combined, alginate-gelatin and calcium chloride gel to form a bioscaffolding in less than 1 second. The resulting gel has a storage modulus of approximately 1 kiloPascal. In application, cell survivability has been observed up to at least 12 days. Encapsulation efficiency is approximately 99%. However, the small pore size of alginate construct systems, which is from about 2 nm to about 500 nm, can lead to low cell spreadability as observed by the round morphology of the hMSC cells over time. "Cell spreading" refers to the naturally occurring morphology of cells. Advantages of alginate construct systems include, but are not limited to, enhanced immune response (a controlled foreign body response) to effect positive remodeling of the injured myocardium, and immunoprotectivity, by shielding via its small pore size, the encapsulated cells from this enhanced immune response (protected from host immune response), instantaneous gelation kinetics, substantial or complete non-adherence to a needle when injected, and long term cell viability. Furthermore, alginate construct systems degrade slowly (at least 8 weeks in vivo).

Fibrin glue can include fibrinogen (modified or not modified with protein constituents) as a first component and thrombin as a second component. In some embodiments, human mesenchymal stems cells (hMSC) are suspended in one component of the gelation system. Fibrin glue systems exhibit fast gelling kinetics, but not as rapid as alginate construct systems. When combined, fibrinogen and thrombin gel to form a bioscaffolding in about 5 seconds to about 10 seconds. The resulting gel has a storage modulus of approximately 3 kiloPascals which is higher than that of alginate construct systems. A higher storage modulus may improve mechanical reinforcement at the infarct region. In application, cell survivability has been observed up to at least 12 days. The pore size of fibrin glue systems is from about 1.5 microns to about 2.5 microns and can lead to high cell spreadability of hMSC cells. That is, hMSC cells have been observed to have an elongate and stellate morphology which is more natural to their endogenous state when compared to the morphology observed in alginate construct systems alone. Advantages of fibrin glue include, but are not limited to, material strength, promotion of angiogenesis, good cytocompatibility (compatible with cell growth), good cell morphology and high cell proliferation in fibrinogen.

The following is a table comparing experimental data and characteristics of alginate construct and fibrin glue systems:

TABLE 1

| Characteristic | 1% Alginate-collagen in 2% CaCl$_2$ | 100% Tisseel ™ (no dilution) |
|---|---|---|
| Pore size | 200-500 nm | 1.5-2.5 μm |
| Storage modulus | 1 kPa | 3 kPa |
| Gelation kinetics | 1 second | 5-10 seconds |
| Encapsulation efficiency | 99.26 ± 0.61 | 93.71 ± 0.61 |
| Morphology | spherical | elongated, spindle-shaped within 24 hours |
| Cell survivability | 12 days to 6 months | at least 12 days |
| Degradation time in vivo | 8 weeks | 2 weeks |

In some embodiments, a bioscaffolding is formed from mixing components of at least two gelation systems. For example, a first component of a first two-component gel and a first component of a second two-component gel can be combined to form a first mixture. A second component of a first two-component gel and a second component of the second two-component gel can be combined to form a second mixture. Cells can be suspended within either the first mixture or the second mixture. When the two mixtures are combined, a bioscaffolding including at least some advantageous characteristics of both gelation systems can be realized. In some embodiments, a bioscaffolding can be formed by mixing at least two different gelation components to form a first mixture. When the first mixture is combined with a gelation salt, a bioscaffolding including at least some advantageous characteristics of the individual components can be realized. It should be appreciated that a number of different combinations of gelation components can be mixed together in different ratios to accentuate various advantageous characteristics of the individual gelation systems. Furthermore, the concentration of the individual components, either singly or combined, can influence certain characteristics of the bioscaffolding, such as viscosity and encapsulation efficiency.

Alginate Construct Systems and Fibrin Glues

Experiment 1 hMSC were suspended in a 1% alginate-collagen solution at $1.43 \times 10^7$ cells/mL. 200 microliters of the alginate-collagen solution was combined with 200 microliters of a thrombin solution containing 40 mM CaCl$_2$. Encapsulation efficiency of the resulting gel was measured at 99.16±0.007%. Encapsulation efficiency was measured as the difference between the initial number of cells in the suspension and the number of cells remaining in the supernatant divided by the initial number of cells and expressed as a percentage. On day 3, the cells exhibited a round morphology. On day 7 and 12, the cells continued to exhibit a round morphology. Cells were analyzed by a molecular probe LIVE/DEAD® Assay available from Invitrogen, Inc. The viscosity of the suspension component was measured at approximately 33 centipoise (cp).

Experiment 2 hMSC were suspended in a thrombin solution containing 40 mM of CaCl2 at a concentration of $2.12 \times 10^7$ cells/mL. A 1% solution of alginate-collagen was combined with the thrombin solution in a 1:1 ratio (200 μL:200 μL). Encapsulation efficiency of the resulting gel was measured at 26.47±5.5%. The viscosity of the suspension component was measured at approximately 7 cp.

Experiment 3

A fibrin glue kit Tisseel™ including modified fibrinogen and thrombin was obtained from Baxter. hMSC were suspended in a thrombin solution at a concentration of $2.96 \times 10^7$ cells/mL. 200 microliters of the thrombin solution containing cells was combined with the fibrinogen solution in a 1:1 ratio. Encapsulation efficiency of the resulting gel was measured at 93.71±3.48%. On day 3, the cells exhibited an elongated, spindle shaped morphology. On day 7 & 12 the cells continued to exhibit similar elongated and spindle shaped morphology and there was visible but no quantitative evidence of cell proliferation. Cells were analyzed by a molecular probe LIVE/DEAD® Assay available from Invitrogen, Inc. The viscosity of the suspension component was measured at approximately 7 cp.

Experiment 4

A fibrin glue kit Tisseel™ including modified fibrinogen and thrombin was obtained from Baxter. Fibrinogen was reconstituted as directed in accompanying instructions and then further diluted with water to half of its original concentration. hMSC were suspended in the reconstituted, full strength thrombin solution at a concentration of $2.96 \times 10^7$ cells/mL. 200 microliters of the thrombin solution containing hMSC was combined with the diluted fibrinogen solution in a 1:1 ratio. Encapsulation efficiency of the resulting gel was measured at 98.07±1.6%. The viscosity of the suspension component was measured at approximately 7 cp.

Experiment 5

A fibrin glue kit Tisseel™ including modified fibrinogen and thrombin was obtained from Baxter. Fibrinogen was reconstituted as directed in accompanying instructions and then further diluted with water to half of its original concentration. hMSC were suspended in the diluted fibrinogen solution at a concentration of $2.96 \times 10^7$ cells/mL. 200 microliters of the diluted fibrinogen solution containing hMSC was combined with the thrombin solution in a 1:1 ratio. Encapsulation efficiency of the resulting gel was measured at 97.12±1.73%. The viscosity of the suspension component was measured at approximately 5 cp.

Experiment 6

A fibrin glue kit Tisseel™ including modified fibrinogen and thrombin was obtained from Baxter. Fibrinogen was reconstituted as directed and then further diluted with water to half of its original concentration. The diluted fibrinogen solution was mixed with a 0.5% alginate-collagen solution in a 1:1 ratio to form a first mixture. hMSC were suspended in a thrombin solution (which contains 40 mM CaCl$_2$) at a concentration of $2.96 \times 10^7$ cells/mL. 200 microliters of the first mixture was combined with the thrombin in a 1:1 ratio. Encapsulation efficiency of the resulting gel was measured at 91.39±6.78%. The viscosity of the suspension component was measured at approximately 7 cp.

Experiment 7

A fibrin glue kit Tisseel™ including modified fibrinogen and thrombin was obtained from Baxter. Fibrinogen was reconstituted as directed and then further diluted with water to half of its original concentration. The diluted fibrinogen solution was mixed with a 0.5% alginate-collagen solution in a 1:1 ratio to form a first mixture. hMSC were suspended in the first mixture at a concentration of $5.51 \times 10^7$ cells/mL. The first mixture was combined with the second mixture comprising thrombin and a 2% CaCl$_2$ solution in a 1:1 ratio. Encapsulation efficiency of the resulting gel was measured at 99.42+0.12%. The viscosity of the suspension component was measured at approximately 6 cp.

Table 2 summarizes the results of a table of experimental data showing the various characteristics of combinations of alginate construct and fibrin glue systems:

TABLE 2

| | First component/first mixture | Second component/second mixture | Encapsulation Efficiency | Component in which cells suspended | Viscosity of component (centipoise) |
|---|---|---|---|---|---|
| 1 | 1% alginate-collagen | Thrombin containing 40 mM $CaCl_2$ | 99.16 ± 0.007 | alginate-collagen | 33.28 ± 2.3 |
| 2 | 1% alginate-collagen | Thrombin containing 40 mM $CaCl_2$ | 26.47 ± 5.5 | thrombin | 7.32 ± 2.6 |
| 3 | Undiluted fibrinogen | Thrombin containing 40 mM CaCl2 | 93.71 ± 3.48 | thrombin | 7.32 ± 2.6 |
| 4 | Diluted fibrinogen | Thrombin containing 40 mM CaCl2 | 98.07 ± 1.6 | thrombin | 7.32 ± 2.6 |
| 5 | Diluted fibrinogen | Thrombin containing 40 mM $CaCl_2$ | 97.12 ± 1.73 | fibrinogen | 5.4 ± 2.8 |
| 6 | Diluted fibrinogen + 0.5% alginate-collagen | Thrombin containing 40 mM $CaCl_2$ | 91.39 ± 6.78 | thrombin | 7.32 ± 2.6 |
| 7 | Diluted fibrinogen + 0.5% alginate-collagen | Thrombin containing 40 mM $CaCl_2$ | 99.42 ± 0.12 | 5% fibrinogen + 0.5% alginate-collagen | 6.5 ± 3.2 |

In one embodiment, a bioscaffolding can be formed by mixing components of more than one gelation system. For example, alginate-gelatin (of an alginate construct system) can be mixed with fibrinogen (of a fibrin glue system) in a 1:1 ratio to form a first mixture. Thrombin (of a fibrin glue system) already contains 40 mM calcium chloride (which is required to gel an alginate construct system) to form a second mixture. Experiments 6 and 7 may represent such a combination. hMSC can be added to an individual component or to the first or second mixture.

Experiment 3 illustrates that, in a standard two-component gelation system which includes a first component (alginate) or a second component (thrombin) only, if the hMSC are suspended in a low viscosity component, i.e., thrombin ($\eta$=7.32±2.6), encapsulation efficiency is very low (E=26.47±5.5%)(i.e., alginate-collagen). However, note that in these experiments, the viscosity of the other component is high and there is a wide mismatch between the two viscosities e.g., the viscosity of 1% alginate-collagen is 33.2%+2.3%. Further, alginate has faster gelation kinetics than the other systems. In experiments 6 and 7 however, even though the hMSC were suspended in a low viscosity component or mixture, the resulting gel showed high encapsulation efficiency. It is theorized that this result is due to the viscosity of the other component being low as well and that there was not much of a mismatch in viscosities between the two components, thus allowing good mixing. Further, the mixed systems gel slower allowing more cell diffusion from the lower viscosity component to the gel. Thus, it has been shown that even if the individual components in which the hMSC is suspended have low viscosities (before gelation), the resulting gel can still exhibit a high encapsulation efficiency (after gelation). This is highly advantageous, as lower viscosity may result in a more successful delivery with a catheter-based delivery system because, for example, such a system requires less force for injection into the infarct region and higher flow rates can be achieved. Additionally, lower viscosity solutions may result in less residual within the lumens of a delivery system. The combination also may provide a high encapsulation efficiency while allowing hMSC to achieve a natural state of morphology, i.e., elongated and spindle shaped. Thus, such a bioscaffolding may include at least some advantageous characteristics of the individual components comprising the two-component gelation systems.

In another embodiment, a bioscaffolding can be formed by mixing alginate-gelatin with sodium-hyaluronate and gelled with calcium chloride. The hyaluronate will be immobilized by chain entanglement and provide attachment ligands for stem cells bearing the CD44 receptor, e.g., human mesenchymal stem cells. Appropriate formulations can have 50% to 99% of a 0.5% to 1.0% solution of alginate-gelatin combined with 1% to 50% of a 0.05% to 1% solution of sodium hyaluronate (Genzyme Biosurgery, Mass.). The mixture can be gelled by the addition of an equal volume of a 0.5% to 1.5% of calcium chloride dihydrate.

In another embodiment, a bioscaffolding can be formed by mixing reconstituted lyophilized peptide (with buffer) with alginate and gelled with calcium chloride. Examples of peptides include self-assembled peptides, such as RAD 16-II (SEQ ID NO: 1), MAX-1 (SEQ ID NO: 2) and EAK16-II (SEQ ID NO: 3). These peptides gel when exposed to conditions of physiological or greater osmolarity, at neutral pH. However, gelation kinetics are relatively slow, ranging from minutes to hours. Introduction of these peptides as a sole scaffold would result in an intercalated structure, at best, due to the slow gelation. Addition of alginate can provide rapid gelation kinetics, thus preventing dissipation of the peptide into tissue.

In some embodiments, a self-assembled peptide (SAP) component can be mixed with a growth factor to form a first mixture. Examples of self-assembled peptides include RAD 16-II (SEQ ID NO: 1), MAX-1 (SEQ ID NO: 2) and EAK16-II (SEQ ID NO: 3). Examples of growth factors in include, but are not limited to, isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). The first mixture can be combined with a component of a two-component gelation system, such as an alginate construct system, a fibrin glue or a polymer system, or any combination thereof. In some embodiments, human mesenchymal stem cells can be added to the system.

In one embodiment, the self-assembled peptide is RAD 16-II (SEQ ID NO: 1) and the growth factor is PDGF or a derivative thereof and combines to form a first mixture. It has been shown that PDGF mediates cardiac microvascular endothelial cell communication with cardiomyocytes and it is anticipated that an application of PDGF can restore damaged endothelial PDGF-regulated angiogenesis and enhance post-ischemic neovascularization in an infarct region. When combined with RAD 16-11 (SEQ ID NO: 1), PDGF binds to RAD 16-II (SEQ ID NO: 1) through weak molecular interactions. In some applications, PDGF remains viable for approximately fourteen days when combined with RAD 16-11 (SEQ ID NO: 1) when applied to an infarct region. However, it is anticipated that the slow kinetics of the self-assembled peptide, i.e., minutes to hours, will cause significant leakage, backflow and dissipation before the peptide can form a nanofiber bioscaffolding at the infarct region.

In some embodiments, the first mixture (comprising RAD 16-II (SEQ ID NO: 1) and PDGF) can be combined with any one component of fibrin glue or an alginate construct. The rapid kinetics of both fibrin glue and alginate constructs can counteract the slow kinetics of the SAP-PDGF construct. It is therefore anticipated that leakage and dissipation at the infarct region can be reduced by combining the SAP-PDGF construct with any one component of fibrin glue or an alginate construct.

Delivery Systems

Devices which can be used to deliver modified or combined components of the gelation systems include, but are not limited to, dual-needle left-ventricle injection devices, dual-needle transvascular wall injection devices and dual syringes. Methods of access to use the minimally invasive (i.e., percutaneous or endoscopic) injection devices include access via the femoral artery or the sub-xiphoid. "Xiphoid" or "xiphoid process" is a pointed cartilage attached to the lower end of the breastbone or sternum, the smallest and lowest division of the sternum. Both methods are known by those skilled in the art.

Figure 2:
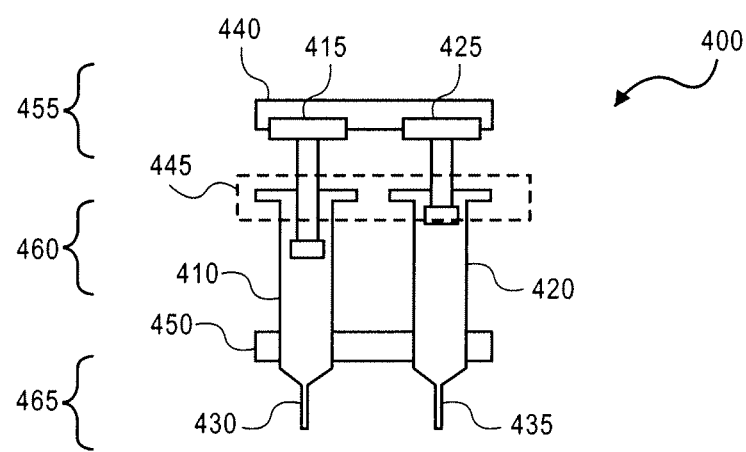
FIG. 2 illustrates an embodiment of a dual bore delivery device.

FIG. 2 illustrates an embodiment of a dual syringe device which can be used to deliver the compositions of the present invention. Dual syringe 400 can include first barrel 410 and second barrel 420 adjacent to one another and connected at a proximal end 455, distal end 460 and middle region 465 by plates 440, 445 and 450, respectively. In some embodiments, barrels 410 and 420 can be connected by less than three plates. Each barrel 410 and 420 includes plunger 415 and plunger 425, respectively. Barrels 410 and 420 can terminate at a distal end into needles 430 and 435, respectively, for extruding a substance. In some embodiments, barrels 410 and 420 can terminate into cannula protrusions for extruding a substance. Barrels 410 and 420 should be in close enough proximity to each other such that the substances in each respective barrel are capable of mixing with one another to form a bioscaffolding in the treatment area, e.g., a post-infarct myocardial region. Dual syringe 400 can be constructed of any metal or plastic which is minimally reactive or completely unreactive with the formulations described in the present invention. In some embodiments, dual syringe 400 includes a pre-mixing chamber attached to distal end 465.

In some applications, first barrel 410 can include a first mixture of a modified two-component gelation system and second barrel 420 can include a second mixture of a modified two-component gelation system according to any of the embodiments described previously. A therapeutic amount of the resulting gel is between about 25 µL to about 200 µL, preferably about 50 µL. Dual syringe 400 can be used during, for example, an open chest surgical procedure.

Figure 3A:
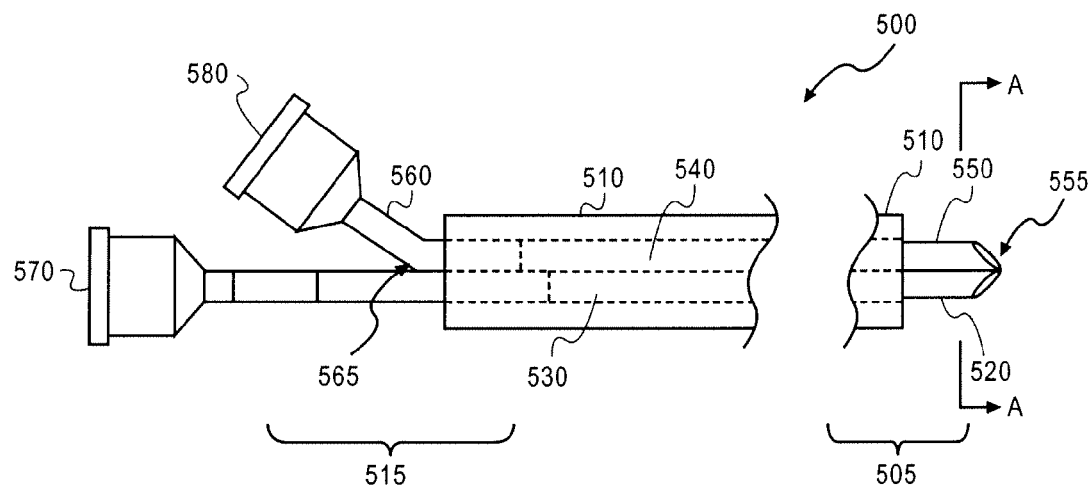
FIGS. 3A-3B illustrate an alternative embodiment of a dual bore delivery device.
Figure 3B:
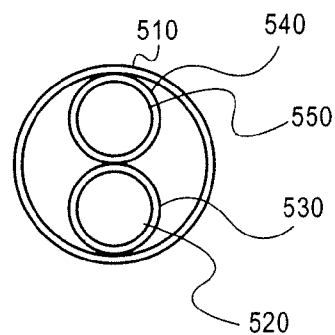

FIGS. 3A-3B illustrate an embodiment of a dual-needle injection device which can be used to deliver the compositions of the present invention. Delivery assembly 500 includes lumen 510 which may house delivery lumens, guidewire lumens and/or other lumens. Lumen 510, in this example, extends between distal portion 505 and proximal end 515 of delivery assembly 500.

In one embodiment, delivery assembly 500 includes first needle 520 movably disposed within delivery lumen 530. Delivery lumen 530 is, for example, a polymer tubing of a suitable material (e.g., polyamides, polyolefins, polyurethanes, etc.). First needle 520 is, for example, a stainless steel hypotube that extends a length of the delivery assembly. First needle 520 includes a lumen with an inside diameter of, for example, 0.08 inches (0.20 centimeters). In one example for a retractable needle catheter, first needle 520 has a needle length on the order of about 40 inches (about 1.6 meters) from distal portion 505 to proximal portion 515. Lumen 510 also includes auxiliary lumen 540 extending, in this example, co-linearly along the length of the catheter (from a distal portion 505 to proximal portion 515). Auxiliary lumen 540 is, for example, a polymer tubing of a suitable material (e.g., polyamides, polyolefins, polyurethanes, etc.). At distal portion 505, auxiliary lumen 540 is terminated at a delivery end of second needle 550 and co-linearly aligned with a delivery end of needle 520. Auxiliary lumen 540 may be terminated to a delivery end of second needle 550 with a radiation-curable adhesive, such as an ultraviolet curable adhesive. Second needle 550 is, for example, a stainless steel hypotube that is joined co-linearly to the end of main needle 520 by, for example, solder (illustrated as joint 555). Second needle 550 has a length on the order of about 0.08 inches (0.20 centimeters). FIG. 3B shows a cross-sectional front view through line A-A' of delivery assembly 500. FIG. 3B shows main needle 520 and second needle 550 in a co-linear alignment.

Referring to FIG. 3A, at proximal portion 515, auxiliary lumen 540 is terminated to auxiliary side arm 560. Auxiliary side arm 560 includes a portion extending co-linearly with main needle 520. Auxiliary side arm 560 is, for example, a stainless steel hypotube material that may be soldered to main needle 520 (illustrated as joint 565). Auxiliary side arm 560 has a co-linear length on the order of about, in one example, 1.2 inches (3 centimeters).

The proximal end of main needle 520 includes adaptor 570 for accommodating a substance delivery device. Adaptor 570 is, for example, a molded female luer housing. Similarly, a proximal end of auxiliary side arm 560 includes adaptor 580 to accommodate a substance delivery device (e.g., a female luer housing).

The design configuration described above with respect to FIGS. 3A-3B is suitable for introducing modified two-component gel compositions of the present invention. For example, a gel may be formed by a combination (mixing, contact, etc.) of a first mixture of a modified two-component gelation system and a second mixture of a modified two-component gelation system. Representatively, a first mixture may be introduced by a one cubic centimeters syringe at adaptor 570 through main needle 520. At the same time or shortly before or after, a second mixture may be introduced with a one cubic centimeter syringe at adaptor 580. When the first and second components combine at the exit of delivery assembly 500 (at an infarct region), the materials combine (mix, contact) to form a bioerodible gel.

Figure 4A:
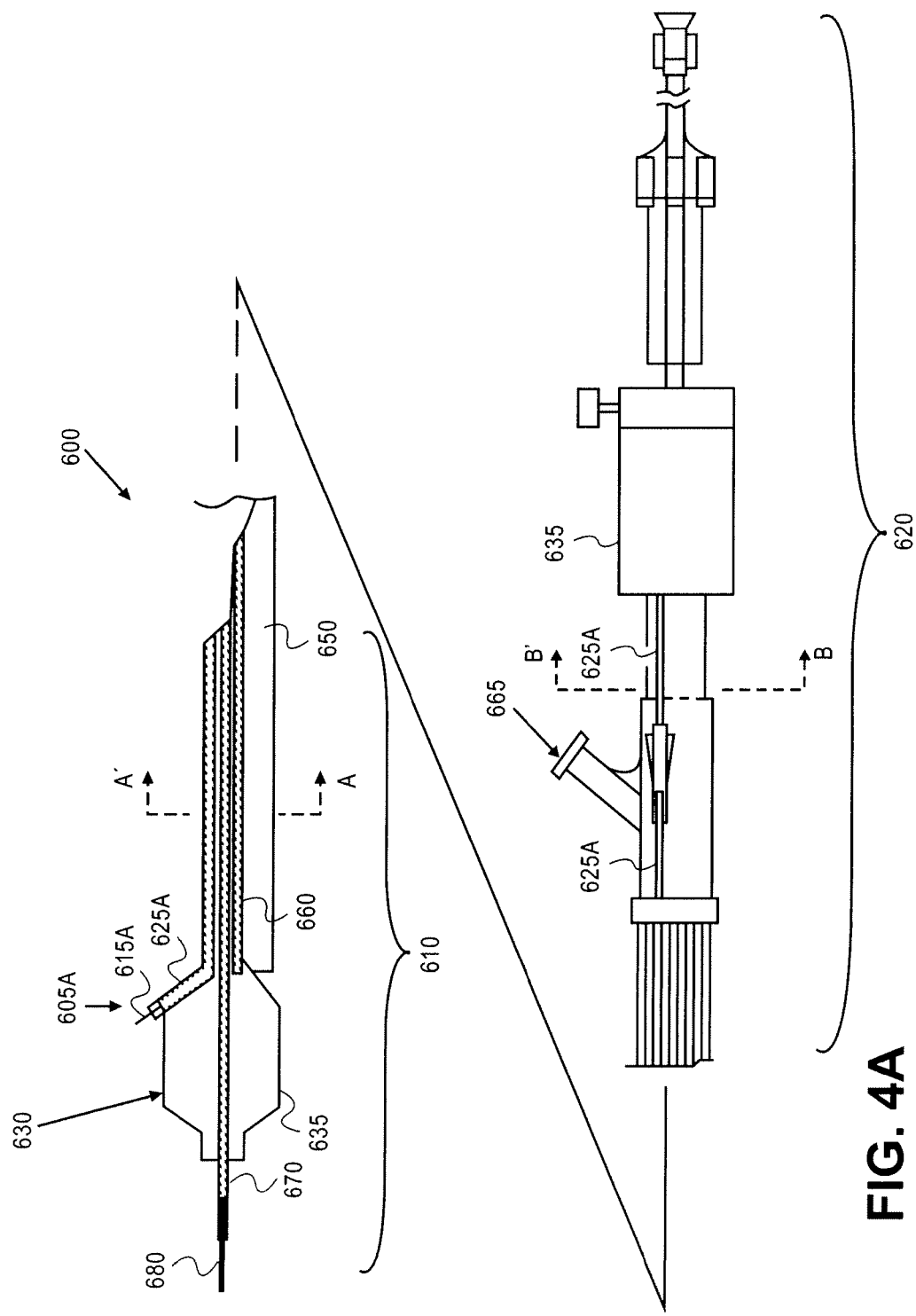
FIGS. 4A-4C illustrate a second alternative embodiment of a dual bore delivery device.
Figure 4B:
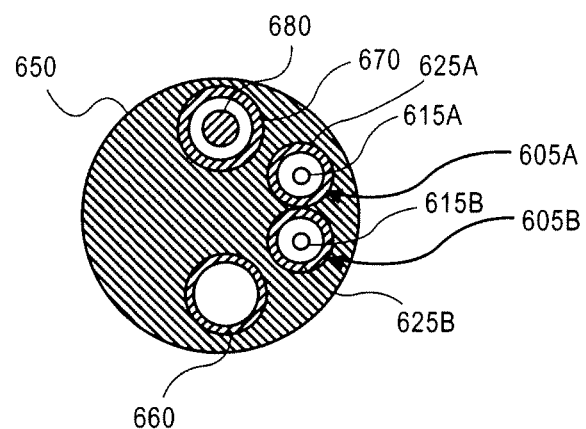
Figure 4C:
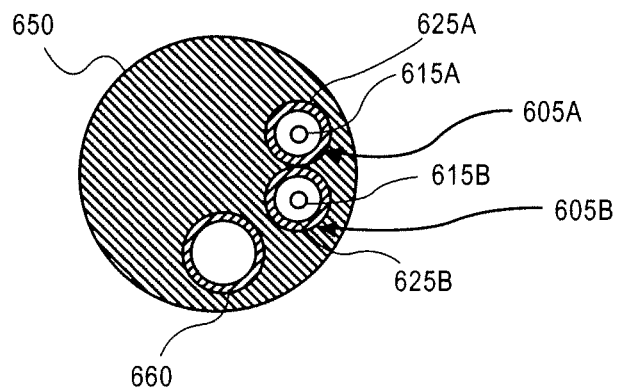

FIGS. 4A-4C illustrate an alternative embodiment of a dual-needle injection device which can be used to deliver two-component gel compositions of the present invention. In general, the catheter assembly 600 provides a system for delivering substances, such as modified two-component gel compositions, to or through a desired area of a blood vessel (a physiological lumen) or tissue in order to treat a myocardial infarct region. The catheter assembly 600 is similar to the catheter assembly described in commonly-owned, U.S. Pat. No. 6,554,801, titled "Directional Needle Injection Drug Delivery Device", which is incorporated herein by reference.

In one embodiment, catheter assembly 600 is defined by elongated catheter body 650 having proximal portion 620 and distal portion 610. Guidewire cannula 670 is formed within catheter body (from proximal portion 610 to distal portion 620) for allowing catheter assembly 600 to be fed and maneuvered over guidewire 680. Balloon 630 is incorporated at distal portion 610 of catheter assembly 600 and is in fluid communication with inflation cannula 660 of catheter assembly 600.

Balloon 630 can be formed from balloon wall or membrane 635 which is selectively inflatable to dilate from a collapsed configuration to a desired and controlled expanded configuration. Balloon 630 can be selectively dilated (inflated) by supplying a fluid into inflation cannula 660 at a predetermined rate of pressure through inflation port 665 (located at proximal end 620). Balloon wall 635 is selectively deflatable, after inflation, to return to the collapsed configuration or a deflated profile. Balloon 630 may be dilated (inflated) by the introduction of a liquid into inflation cannula 660. Liquids containing treatment and/or diagnostic agents may also be used to inflate balloon 630. In one embodiment, balloon 630 may be made of a material that is permeable to such treatment and/or diagnostic liquids. To inflate balloon 630, the fluid can be supplied into inflation cannula 660 at a predetermined pressure, for example, between about one and 20 atmospheres. The specific pressure depends on various factors, such as the thickness of balloon wall 635, the material from which balloon wall 635 is made, the type of substance employed and the flow-rate that is desired.

Catheter assembly 600 also includes at least two substance delivery assemblies (not shown; see FIGS. 4B-4C) for injecting a substance into a myocardial infarct region. In one embodiment, substance delivery assembly 605a includes needle 615a movably disposed within hollow delivery lumen 625a. Delivery assembly 605b includes needle 615b movably disposed within hollow delivery lumen 625b (not shown; see FIGS. 4B-4C). Delivery lumen 625a and delivery lumen 625b each extend between distal portion 610 and proximal portion 620. Delivery lumen 625a and delivery lumen 625b can be made from any suitable material, such as polymers and copolymers of polyamides, polyolefins, polyurethanes and the like. Access to the proximal end of delivery lumen 625a or delivery lumen 625b for insertion of needle 615a or 615b, respectively is provided through hub 635 (located at proximal end 620). Delivery lumens 625a and 625b may be used to deliver first and second mixtures of a modified two-component gel composition to a post-myocardial infarct region.

FIG. 4B shows a cross-section of catheter assembly 600 through line A-A' of FIG. 4A (at distal portion 610). FIG. 4C shows a cross-section of catheter assembly 600 through line B—B' of FIG. 4A. In some embodiments, delivery assemblies 605a and 605b are adjacent to each other. The proximity of delivery assemblies 605a and 605b allows each mixture of the modified two-component gelation system to rapidly gel when delivered to a treatment site, such as a post-myocardial infarct region.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A composition comprising:
   a first mixture comprising a first component of a first two-component gel system and a first component of a second two-component gel system,
   wherein the first component of the first two component gel system is one of an alginate-collagen, an alginate-laminin, an alginate-elastin, an alginate-collagen-laminin, an alginate-hyaluronic acid, an alginate and a self-assembled peptide, and wherein the first component of the second two-component gel system is one of fibrinogen, a fibrinogen conjugate, and sodium hyaluronate, and
   a second mixture comprising a second component of the first two-component gel system and a second component of the second two-component gel system, wherein the second component of the first two-component gel system is one of sodium chloride, calcium chloride, barium chloride, strontium chloride and sucrose, and wherein the second component of the second two-component gel system is different than the second component of the first two-component gel system, and is one of thrombin and sucrose, and
   wherein upon separately injecting the first mixture and the second mixture into a post-myocardial infarction area of a heart, the first component and the second component of the first two-component gel system mix to form a first gel and the first component and the second component of the second two-component gel system mix to form a second gel, and
   wherein the first gel has a different characteristic than the second gel.

2. The composition of claim 1, further comprising at least one cell type suspended in one of the first mixture or the second mixture.

3. The composition of claim 2, wherein the cell type is selected from the group consisting of localized cardiac progenitor cells, mesenchymal stem cells, bone marrow derived mononuclear cells, adipose stem cells, embryonic stem cells, umbilical cord blood derived stem cells, smooth muscle cells and skeletal myoblasts.

4. The composition of claim 2, further comprising at least one growth factor in one of the first mixture or the second mixture.

5. The composition of claim 4, wherein the growth factor is selected from the group consisting of vasoendothelial growth factor, fibroblast growth factor, Del 1, hypoxia inducing factor, monocyte chemoattractant protein, nicotine, platelet derived growth factor, insulin-like growth factor 1, transforming growth factor, hepatocyte growth factor, estrogens, follistatin, proliferin, prostaglandin E1 and E2, tumor necrosis factor, interleukin 8, hematopoietic growth factors, erythropoietin, granulocyte-colony stimulating factors and platelet-derived endothelial growth factor.

6. The composition of claim 1, wherein the first component of the first two-component gel system and the second component of the second two-component gel system is mixed in a one-to-one ratio.

7. The composition of claim 1, wherein (a) the first component of the first two-component gel system is an alginate-collagen solution and the first component of the second two-component gel system is a fibrinogen solution and (b) the second component of the first two-component gel system is a 2.0% mass per volume calcium chloride solution and the second component of the second two-component gel system is a thrombin solution.

8. The composition of claim 7, further comprising human mesenchymal stem cells suspended in one of the first mixture or the second mixture.

9. The composition of claim 7, wherein the concentration of alginate-collagen is in a range from between 0.5% mass per volume to 1.0% mass per volume.

10. The composition of claim 7, wherein the concentration of fibrinogen is in a range from between 5.0% mass per volume to 7.0% mass per volume.

11. The composition of claim 7, wherein the concentration of thrombin is in a range from between 9.5% mass per volume to 10.0% mass per volume.

12. The composition of claim 7, wherein the alginate-collagen and fibrinogen are mixed in a one-to-one ratio.

13. The composition of the claim 7, wherein the thrombin and calcium chloride are mixed in a one-to-one ratio.

14. The composition of claim 1, wherein (a) the first component of the first two-component gel is a self-assembled peptide and the first component of the second two-component gel is fibrinogen and (b) the second component of the first two-component gel is 2.0% mass per volume calcium chloride and the second component of the second two-component gel is thrombin.

15. The composition of claim 14, further comprising platelet derived growth factor combined with the self-assembled peptide.

16. The composition of claim 14, wherein the self-assembled peptide is selected from the group consisting of RAD 16-II (SEQ ID NO: 1), MAX-1 (SEQ ID NO: 2) and EAK16-II (SEQ ID NO: 3).

* * * * *

SEQUENCE LISTING

```
<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: Self-assembled peptides

<400> SEQUENCE: 1

Arg Ala Arg Ala Asp Ala Asp Ala Arg Ala Arg Ala Asp Ala Asp Ala
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: Self-assembled peptides

<400> SEQUENCE: 2

Val Lys Val Lys Val Lys Val Lys Val Pro Pro Thr Lys Val Lys Val
```

```
1               5               10              15
Lys Val Lys Val
                20

<210> SEQ ID NO 3
<211> LENGTH: 16
<212> TYPE: PRT
<213> ORGANISM: Artificial Sequence
<220> FEATURE:
<223> OTHER INFORMATION: Self-assembled peptides

<400> SEQUENCE: 3

Ala Glu Ala Glu Ala Lys Ala Lys Ala Glu Ala Glu Ala Lys Ala Lys
1               5                   10                  15
```